United States Patent
Song et al.

(10) Patent No.: US 6,508,757 B1
(45) Date of Patent: Jan. 21, 2003

(54) ATTACHMENT TO FLEXIBLE BRONCHOSCOPE, SLOTTED TUBULAR STYLET FOR ENDOTRACHEAL INTUBATION

(76) Inventors: Paul Huan Song, 1229 S. Electric Ave., Alhambra, CA (US) 91803; Jing Song, 35 Jenna La., Staten Island, NY (US) 10304

( * ) Notice: Subject to any disclaimer, the term of this patent is extended or adjusted under 35 U.S.C. 154(b) by 75 days.

(21) Appl. No.: 09/695,573

(22) Filed: Oct. 23, 2000

Related U.S. Application Data (60) Provisional application No. 60/161,509, filed on Oct. 25, 1999.

(51) Int. Cl.⁷ .................................. A61B 1/24
(52) U.S. Cl. ....................................... 600/120
(58) Field of Search ................... 600/120, 125

(56) References Cited

U.S. PATENT DOCUMENTS

| | | | |
|---|---|---|---|
| 5,327,881 A | * 7/1994 | Greene | 600/120 |
| 5,431,152 A | * 7/1995 | Flam et al. | 600/120 |
| 5,607,386 A | * 3/1997 | Flam | 600/120 |
| 5,733,241 A | * 3/1998 | King | 600/125 |
| 5,921,917 A | * 7/1999 | Barthel et al. | 600/120 |

* cited by examiner

Primary Examiner—Gerald A. Michalsky (57) ABSTRACT

A cost-effective fiberoptic endotracheal intubation aid that comprises a petalled tubular stylet, a medial member and a compress device is disclosed. The petalled tubular stylet is a section of tube made of malleable material and has a proximal end splitted into multiple longitudinal petals of certain length. The medial member is a resilient thin flat sheet with edge curb and the compress device is a clamp-like device. Such an intubation aid can be easily used in combination with conventional flexible fiberoptic bronchoscope and conventional endotracheal tube (E.T.). It will make the flexible insertion probe of F.O. bronchoscope as firm, preformable and manipulatable as a regular solid-wire stylet. Intubators using the present invention are able to visualize patient's pharynx area and simultaneously manipulate the tubular stylet for guiding E.T. into patient's trachea to a desired location.

10 Claims, 7 Drawing Sheets

Assembly that includes the INSERTION PROBE, TUBULAR STYLET and MEDIAL MEMBER, is as one unit being withdrawn from the E.T., after the E.T. has been guided into patient's trachea to a desired location.

FIG.7

ATTACHMENT TO FLEXIBLE BRONCHOSCOPE, SLOTTED TUBULAR STYLET FOR ENDOTRACHEAL INTUBATION

CROSS REFERENCE TO RELATED APPLICATIONS

This application claims the benefit of provisional application, Ser. No. 60/161,509, filed Oct. 25, 1999.

STATEMENT REGARDING FEDERALLY SPONSORED RESEARCH OR DEVELOPMENT

This invention is not a result from federally sponsored research or development.

BACKGROUND OF THE INVENTION

Endotracheal intubation plays an important role in airway management. Failure to maintain a patient's airway for a few minutes may result in serious consequence:brain damage even death.

Difficult endotracheal intubation is often a problem in anesthetic unit or intensive care unit of a hospital when trying to intubate unconscious patients or patients whose epiglotis and vocal cords can not be seen directly by the physician due to abnormal anatomical or pathological condition.

Usual practice to facilitate difficult endotracheal intubation involves using flexible fiberoptic bronchoscope to visualize a patient's pharynx area. But draw-back of this usual practice is the lack of manoeuvrability of endotracheal tube(E.T.).

Such manoeuvrability is very much needed for guiding E.T. into patient's trachea, but a flexible fiberoptic bronchoscope alone does not have the rigidity to provide such manoeuvrability.

A compromised method had been suggested: a regular solid-wire intubation stylet and the insertion probe of flexible fiberoptic bronchoscope are parallelly put into a conventional E.T., in order to simultaneously obtain manoeuvrability of E.T. and visualization of patient's pharynx area. But such method requires a much larger than usual E.T. to accommodate both the insertion probe and solid-wire stylet in parallel. Quite often a much larger E.T. is unacceptable due to patient's age, size and clinical condition.

Several intubation aids have been described in recent years, but they are either complicated or expensive. Most of them are of specialized design and not to be used in combination with popular instruments in hospitals: conventional E.T. and conventional flexible fiberoptic bronchoscope.

Much effort had been made to create an inexpensive and effective endotracheal intubation aid which can be used in combination with conventional flexible fiberoptic bronchoscope but does not require much larger conventional E.T., and will make the insertion probe of the flexible fiberoptic bronchoscope as firm, preformable and manipulatable as a regular solid-wire intubation stylet that intubators are familiar with.

In recent years, several US patents that tried to solve such problem had been issued:

1. U.S. Pat. No. 5,058,577-Gary Six
2. U.S. Pat. No. 5,327,881-Christopher M. Greene
3. U.S. Pat. No. 5,431,152-Gary H. Flam
4. U.S. Pat. No. 5,607,386-Gary H. Flair
5. U.S. Pat. No. 5,733,241-Geoge H. King
6. U.S. Pat. No. 5,921,917-Thomas C. Barthel

BRIEF SUMMARY OF THE INVENTION

The present invention provides a cost-effective intubation aid that includes a petalled tubular stylet, a medial member, and a compress device.When used in combination with conventional endotracheal tube(E.T.) and conventional flexible fiberoptic bronchoscope, the present invention will make the insertion probe of flexible fiberoptic bronchoscope as firm, preformble and manipulatable as a regular solid-wire stylet. Hence it will simultaneously provide manoeuvrability of E.T. and visualization of patient's pharynx area, so as to facilitate difficult endotracheal intubations.

The petalled tubular stylet is made of non-toxic malleable material and manufactured to have smooth surface and edges.

The proximal end of petalled tubular stylet is split into multiple longitudinal petals of certain length. Total number of petals is recommended to be 3 to 12, and at least one petal must be properly dimensioned to be easily bent outward.

When such petalled tubular stylet is put inside a conventional E.T., the properly dimensioned or, so to speak, selected petal can be bent outward and folded onto the outside surface of E.T., to maintain the position of distal end of petalled tubular stylet relative to distal end of E.T.

The insertion probe of a conventional flexible fiberoptic bronchoscope usually includes fiberoptic bundles, insufflation channel and tip control wires. Such an insertion probe is wrapped around by the medial member, then both are put into the petalled proximal end of the petalled tubular stylet. The medial member will be at petalled proximal end, and the tip of insertion probe will pass through the distal end of the petalled tubular stylet.

The medial member is made of non-toxic resilient material, and when inwardly pressed by the compress device, it will frictionally engage the insertion probe to the petalled tubular stylet, and keep the tip of insertion probe in proper position relative to the distal end of petalled tubular stylet.

When the present invention is used in combination with a conventional flexible fiberoptic bronchoscope and a conventional E.T., the petalled tubular stylet will provide proper rigidity and manipulatability for guiding the E.T. into patient's trachea to a desired location, according to the view seen by the intubator using the flexible fiberoptic bronchoscope, on a monitor screen or via an eye-piece.

BRIEF DESCRIPTION OF DRAWINGS

NOTE: a. Exemplified dimensions of a product model—A= 320 MM, B=80 MM, C=5.5 MM, D=6.5 MM, E=0.5 MM, F=1.8 MM.

b. The above dimensions may be different for various models or applications.

NOTE: a. Exemplified dimensions of a product model—H= 25 MM, I=1.0 MM, J=28 MM, L=0.25 MM, K=1.25 MM.

b. The above dimensions may be different for various models or applications.

14—a conventional E.T.

16—PETALLED TUBULAR STYLET of the present invention.

18—MEDIAL MEMBER of the present invention.

20—a longitudinal petal of PETALLED TUBULAR STYLET(16) folded onto outside surface of E.T.(14).

22—Tip of insertion probe(12), protruded out of the distal end of PETALLED TUBULAR STYLET(16).

24—COMPRESS DEVICE of the present invention.

FIG. 4A is a side view of the assembly of FIG. 4, where a selected petal is shown.When installing the COMPRESS DEVICE(24), the selected petal(20) is pre-pushed aside beyond the pressing area of COMPRESS DEVICE. Such selected petal can be, further bent outward and folded onto outside surface of E.T.(14), as a measure to maintain proper relative position.

NOTE: a. Exemplified dimensions of a product model—A= 320 MM, B=80 MM, C=5.5 MM, D=6.5 MM, E=0.5 MM, F=1.8 MM.

b. The above dimensions may be different for various models or applications.

DETAILED DESCRIPTION OF THE INVENTION

The present invention comprises: a petalled tubular stylet, a medial member and a compress device.

The object of the present invention is to provide a cost-effective endotracheal intubation aid which can easily be used in combination with a conventional flexible fiberoptic bronchoscope & a conventional endotracheal tube(E.T.), and make the insertion probe of flexible fiberoptic bronchoscope as firm, preformable and manipulatable as a regular solid-wire intubation stylet.

The present invention will enable the intubator to visualize patient's larynx and pharynx area during endotracheal intubation, and simultaneously maneuver the E.T. that envelopes the petalled tubular stylet, in the same easy way as handling a regular solid-wire stylet.

Figure 1:
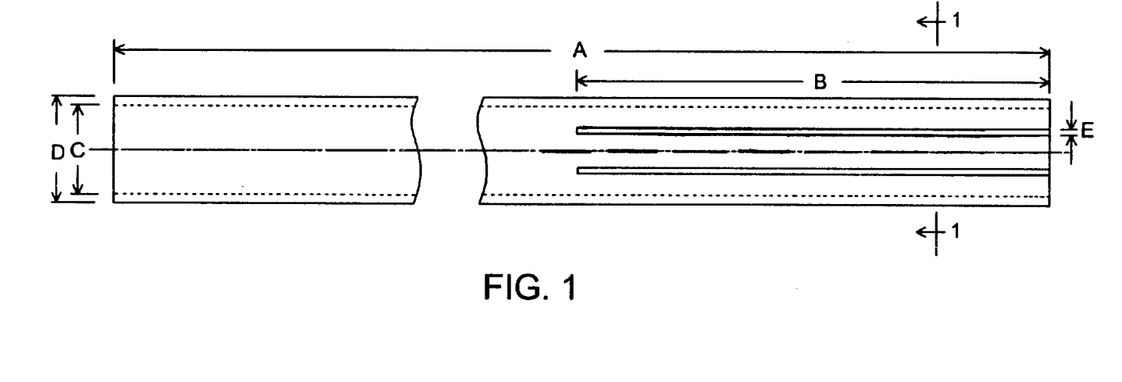
FIG. 1 is a general view of a preferred embodiment of PETALLED TUBULAR STYLET in accordance with the present invention which has three longitudinal petals including one outward-bendable petal.
Figure 1A:
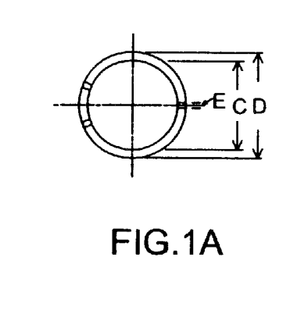
FIG. 1A is a cross-sectional view of the PETALLED TUBULAR STYLET of FIG. 1, taken at lines 1—1.
Figure 2:
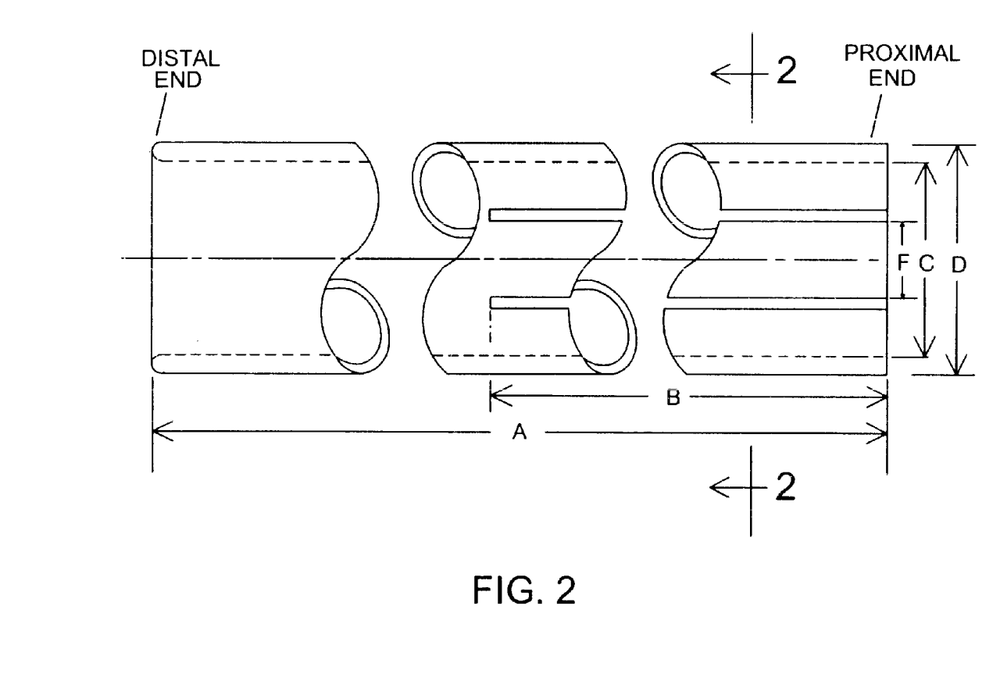
FIG. 2 is an enlarged view of proximal end and distal end of a preferred embodiment of PETALLED TUBULAR STYLET which has two wider petals and one narrow outward-bendable petal at proximal end, in accordance with the present invention.
Figure 2A:
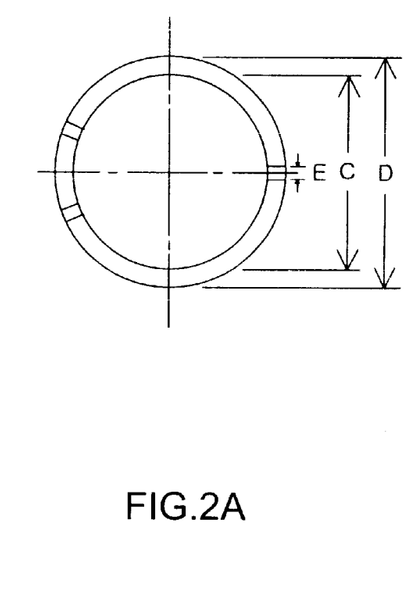
FIG. 2A is a cross-sectional view of the PETALLED TUBULAR STYLET of FIG. 2, taken at lines 2—2.

The petalled tubular stylet of the present invention is made of non-toxic malleable material. It has smooth surface & edges, and its proximal end is splitted into multiple longitudinal petals of certain length. When placed inside a conventional E.T., one of the longitudinal petals of the petalled tubular stylet can be bent outward at a distance as needed, and folded onto the outside surface of E.T., as a means to maintain the position of distal end of petalled tubular stylet relative to distal end of E.T., refer to FIG. 1 and FIG. 4.

The insertion probe of a conventional flexible fiberoptic bronchoscope usually includes fiberoptic bundles, insufflation channel and tip-control wires. Such an insertion probe is wrapped around by a medial member and threaded from proximal end to distal end of the petalled tubular stylet, with the wrapping medial member at proximal end. The tip of insertion probe is allowed to pass through, and protrude out of the distal end of the petalled tubular stylet for a small distance which depends on the need of application and usually is a few milli-meters.

The medial member is made of non-toxic resilient material and used to engage the petalled tubular stylet to the insertion probe of flexible fiberoptic bronchoscope. A compress device is installed around the petalled end of the petalled tubular stylet. The medial member, when placed beneath the petalled end and inwardly pressed, will tightly contact the inner surfaces of the longitudinal petals of petalled tubular stylet and the outer surface of the insertion probe of flexible fiberoptic bronchoscope, so these three items will be frictionally engaged together.

Figure 3:
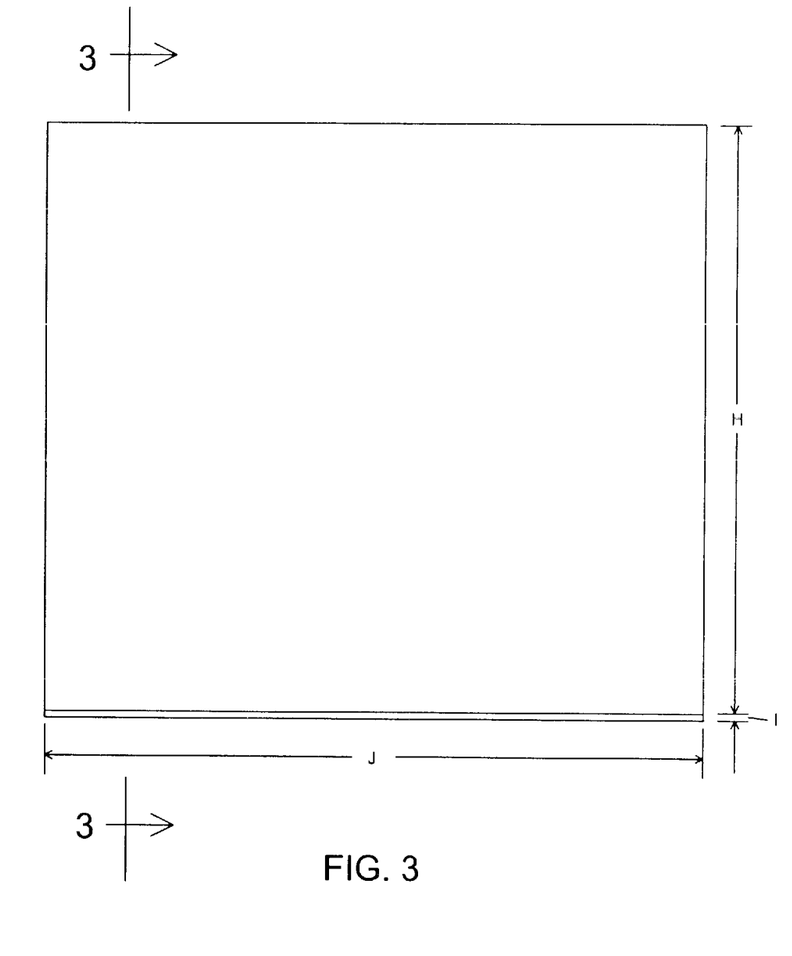
FIG. 3 is an enlarged view of a preferred embodiment of MEDIAL MEMBER in accordance with the present invention, a thin flat sheet with edge curb.
Figure 3A:
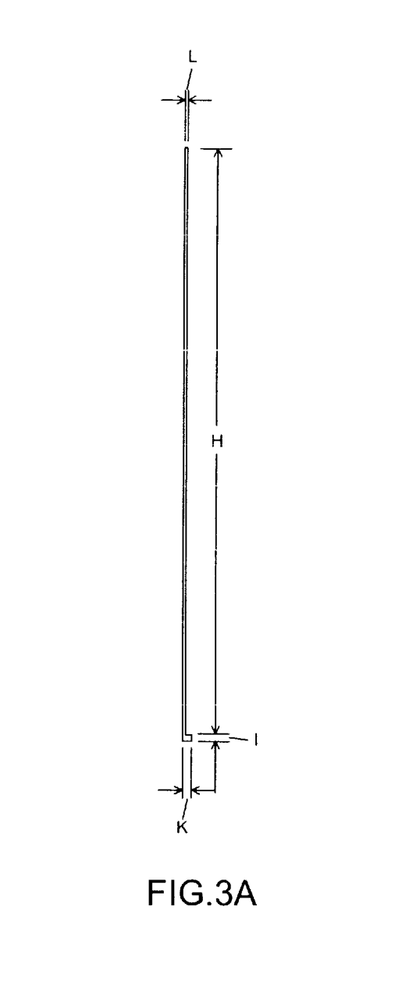
FIG. 3A is a cross-sectional view of the MEDIAL MEMBER of FIG. 3, taken at lines 3—3.

A preferred embodiment of medial member is a thin flat sheet with a tiny edge-curb, as in FIG. 3 and FIG. 3A, to be cut to meet the requirements of various applications.

Figure 4:
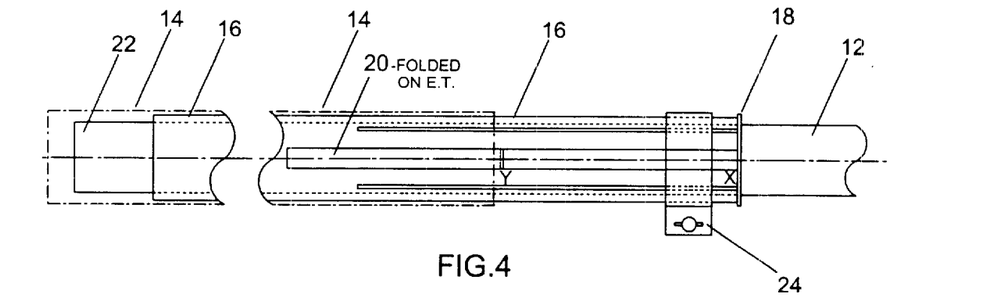
FIG. 4 shows the assembly that comprises: a conventional flexible fiberoptic bronchoscope, a conventional endotracheal tube(E.T.) and elements of the present invention (PETALLED TUBULAR STYLET, MEDIAL MEMBER & COMPRESS DEVICE), Where: 12—Insertion probe of a conventional flexible fiberoptic bronchoscope.
Figure 4A:
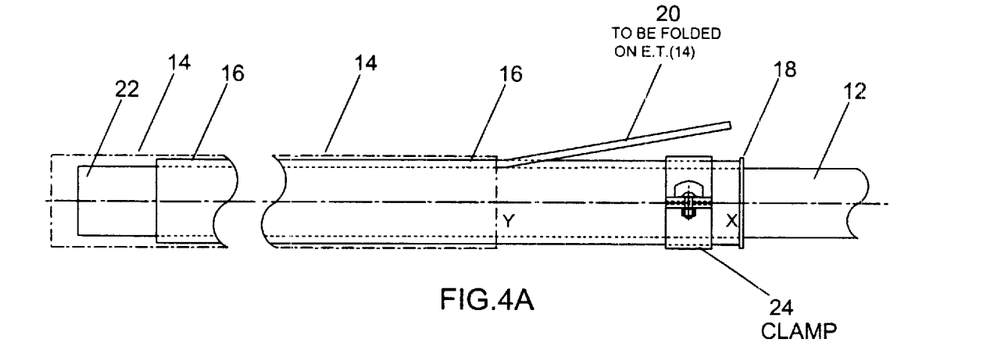

FIG. 4 and FIG. 4A show an assembly which comprises a conventional flexible fiberoptic bronchoscope, a conventional E.T., and PETALLED TUBULAR STYLET, MEDIAL MEMBER & COMPRESS DEVICE of the present invention.

Proper position adjustments need to be accomplished, such as adjustment of the position of distal end of insertion probe relative to distal end of petalled tubular stylet, and adjustment of the position of distal end of petalled tubular stylet relative to distal end of E.T.

Figure 4B:
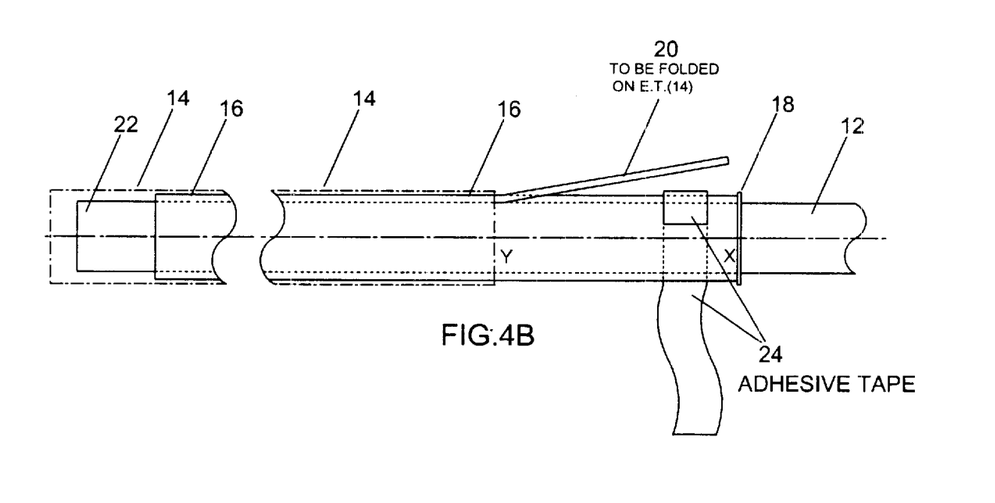
FIG. 4B is a similar side view as FIG. 4A, with the exception that medical adhesive tape or VELCRO tape is used instead of a clamp-like COMPRESS DEVICE.
Figure 5:
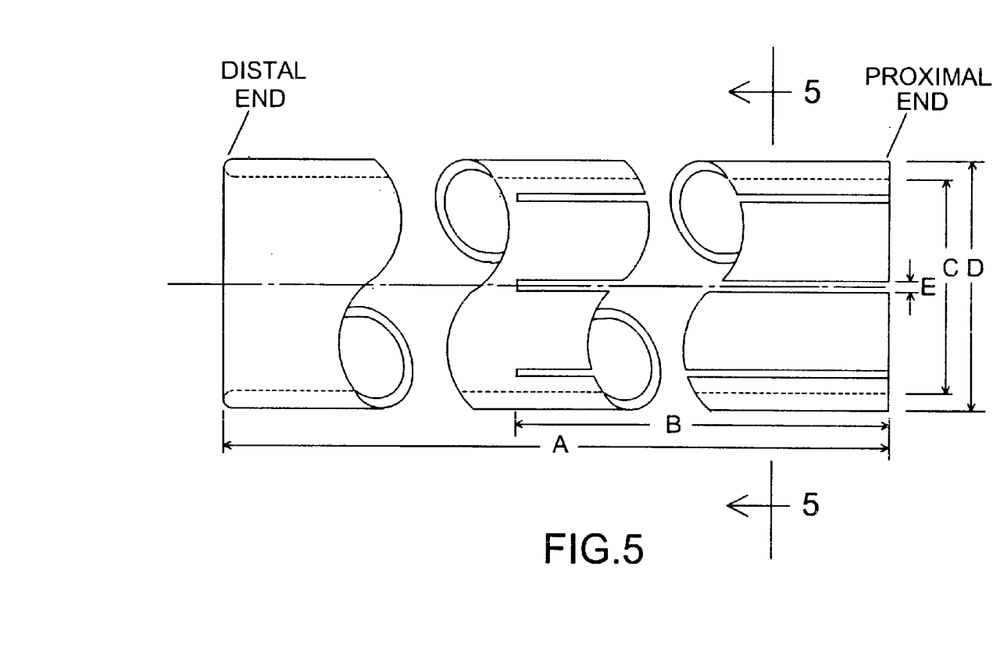
FIG. 5 is another preferred embodiment of PETALLED TUBULAR STYLET with multiple petals at proximal end. One of the petals can be bent outward and folded on an E.T.
Figure 5A:
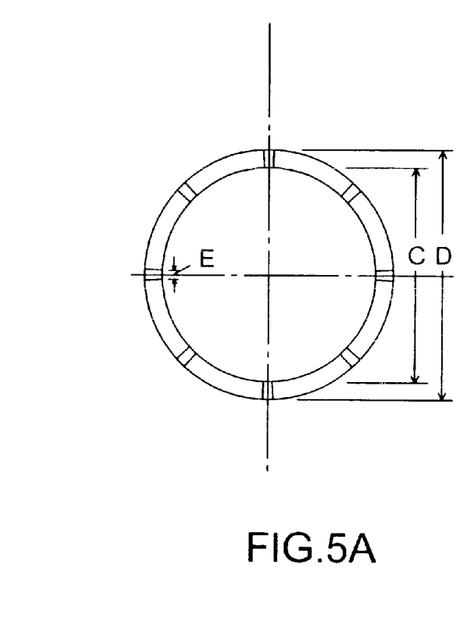
FIG. 5A is a cross-sectional view of the PETALLED TUBULAR STYLET of FIG. 5, taken at lines 5—5.
Figure 6:
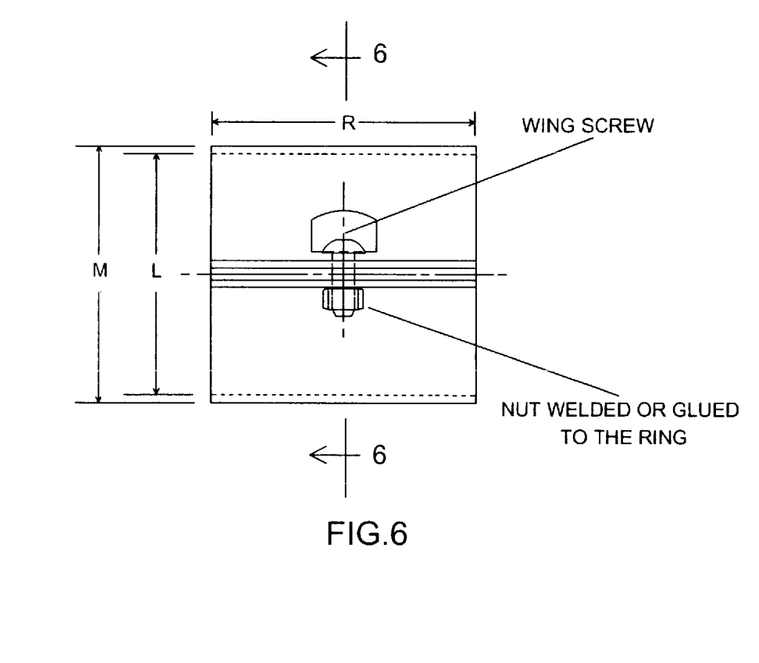
FIG. 6 is a general view.of a preferred embodiment of COMPRESS DEVICE in accordance with the present invention.
Figure 6A:
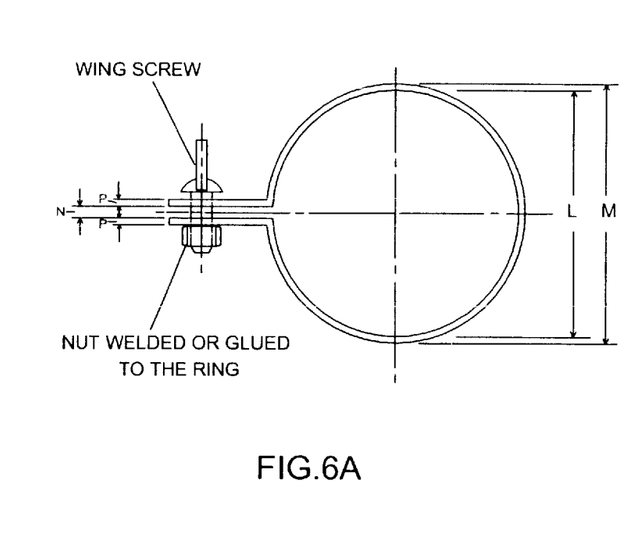
FIG. 6A is a cross-sectional view of COMPRESS DEVICE of FIG. 6, taken at lines 6—6.
Figure 7:
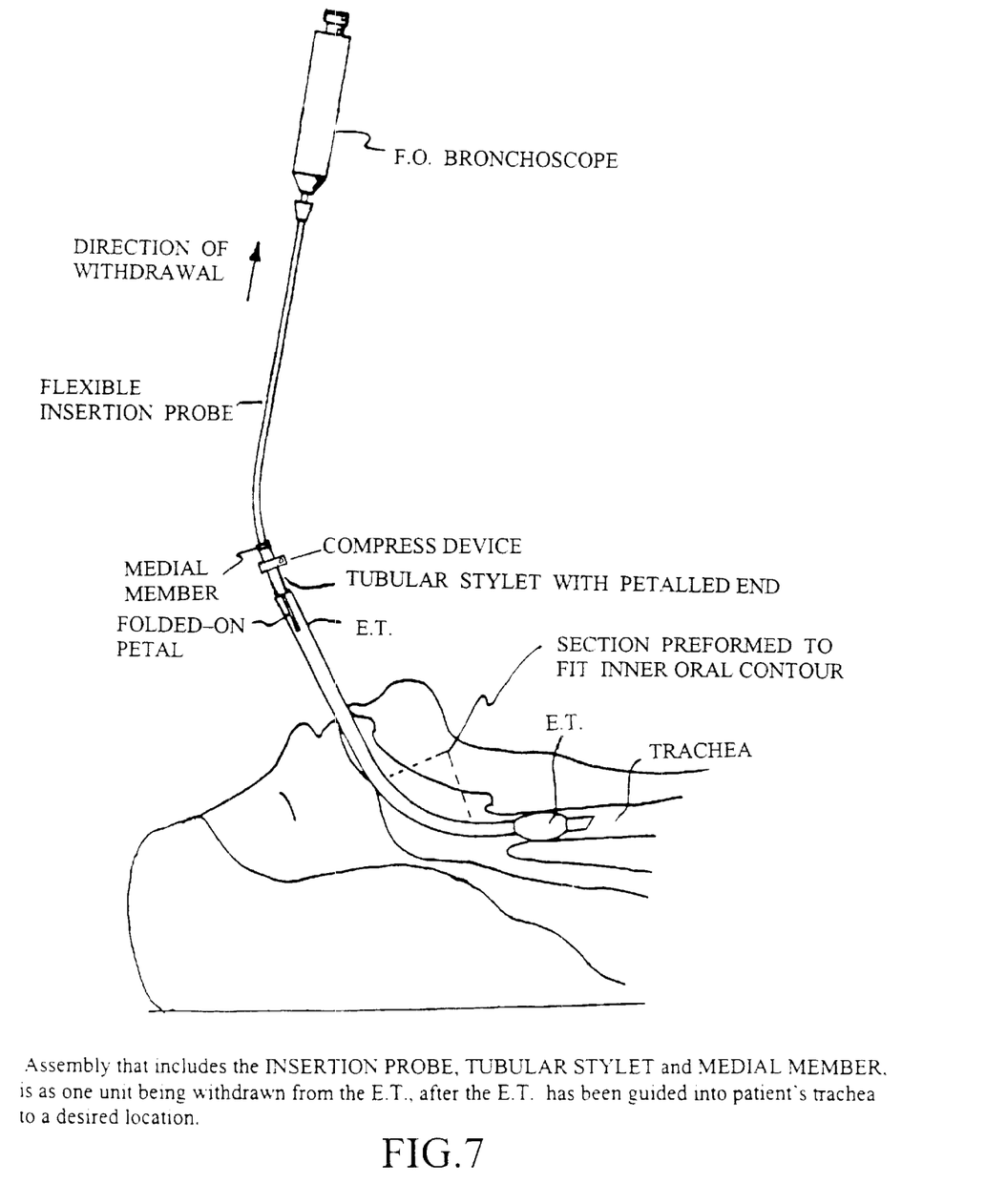
FIG. 7 is a general view during endotracheal intubation.

When petalled tubular stylet, medial member and flexible insertion probe of a F.O. bronchoscope are assembled as one unit, a compress device is used at petalled end to inwardly press the longitudinal petals of tubular stylet, in order that the three items(petalled tubular stylet, medial member and the flexible insertion probe) are squeezed and engaged together. Such compress device may be a clamp attached to petalled end of petalled tubular stylet, refer to FIG. 4, and may also be layer(s) of medical adhesive tape or VELCRO tape manually pressed and wrapped around the petalled end, refer to FIG. 4B, after proper adjustment of relative position of distal ends has been done.

Adjustment of position of petalled tubular stylet's distal end relative to E.T.'s distal end can be accomplished by pushing or pulling the petalled tubular stylet in the E.T. When relative position requirement is met, the pre-pushed-out selected longitudinal petal of the petalled tubular stylet will be further bent outward and folded onto outside surface of E.T., as Y in FIG. 4, to maintain the achieved proper relative position.

Section X-Y of the petalled tubular stylet, as in FIG. 4, serves as a handle for the intubators to guide the E.T. into patient's trachea by manipulating the petalled tubular stylet, just like handling a regular solid-wire stylet.

When the E.T. has been guided into patient's trachea to a desired location, the assembly which includes the insertion probe of flexible fiberoptic bronchoscope and all components of this invention (12, 16, 18 & 24 in FIG. 4) will be withdrawn as one unit, then the E.T. (14 in FIG. 4) will be left in patient's trachea.

However, even before E.T. has been guided into patient's trachea, the insertion probe of flexible fiberoptic bronchoscope in such assembly is already available for oxygen insufflation, drug administration, jet ventilation and secretion removal.

The petalled tubular stylet together with the E.T. that envelopes it, can be preformed to a required shape to fit patient's inner oral contour, before being put in patient's mouth for intubation.

We claim:

1. An attachment to flexible fiberoptic scope for facilitating endotracheal intubation, comprising:

A petalled tubular stylet having a proximal end split into multiple longitudinal petals, a smooth distal end and a longitudinal interior passage extending therethrough;

A medial member wrapping around the flexible insertion probe of fiberoptic scope and both being threaded through said petalled tubular stylet with said wrapping medial member at and beneath petalled end of said petalled tubular stylet, and tip of said insertion probe protruded a small distance out of distal end of said petalled tubular stylet;

A compress device being installed outside and around the petalled end of said petalled tubular stylet as a means to apply inward pressure for squeezing and frictionally engaging the insertion probe of fiberoptic scope, said medial member and said petalled tubular stylet together as a firm, malleable and manipulatable assembly;

Said assembly when placed inside an endotracheal tube being slid to reach a proper relative position of their distal ends and one selected petal of said petalled tubular stylet being bent outward and folded onto outside surface of endotracheal tube to maintain the achieved proper relative position; and Said assembly when placed inside an endotracheal tube being able to simultaneously provide visualization of patient's pharynx area due to images transmitted by fiberoptic insertion probe and manoeuvrability of endotracheal tube due to manipulation of said petalled tubular stylet for guiding endotracheal tube into patient's trachea to a desired location.

2. Said petalled tubular stylet, as recited in claim 1, has a petalled end split into multiple longitudinal petals of definite length and at least one of the petals is properly dimensioned to be bent outward and folded onto the outside surface of an endotracheal tube enveloping said petalled tubular stylet during endotracheal intubation.

3. The longitudinal petals of said petalled tubular stylet, as recited in claim 1, can be inwardly pressed by a compress device via medial member onto the flexible insertion probe of a fiberoptic scope in order to engage these items together.

4. Said petalled tubular stylet, as recited in claim 1, is made of non-toxic malleable material.

5. Said petalled tubular stylet, as recited in claim 1, is manufactured to have smooth surface and edges.

6. Said medial member, as recited in claim 1, is made of non-toxic resilient material.

7. A preferred embodiment of said medial member, as recited in claim 1, is a thin flat sheet with an edge curb.

8. Said compress device, as recited in claim 1, is made of medically acceptable material and to be used to compress the petalled end of said petalled tubular stylet for applying inward pressure through medial member onto the flexible insertion probe of fiberoptic scope.

9. The function of said compress device, as recited in claim 8, can also be achieved by pressing and wrapping medical adhesive tape around the petalled end of said petalled tubular stylet.

10. Said compress device, as recited in claim 1, is securely attached to said petalled tubular stylet, in order that it would not break free from said petalled tubular stylet and drop into patient's mouth during intubation.

\* \* \* \* \*